United States Patent [19]

Tung et al.

[11] Patent Number: 5,780,691
[45] Date of Patent: Jul. 14, 1998

[54] PROCESS FOR PRODUCING 1,1,1,2,3,3,3,-HEPTAFLUOROPRANE

[75] Inventors: Hsueh Sung Tung, Getzville; Lois Anne Ellis, Orchard Park, both of N.Y.

[73] Assignee: Allied Signal Inc., Morristown, N.J.

[21] Appl. No.: 772,683

[22] Filed: Dec. 23, 1996

[51] Int. Cl.$^6$ .................... C07C 17/06; C07C 19/08
[52] U.S. Cl. .................. 570/134; 570/161; 570/164
[58] Field of Search ......................... 570/134, 161, 570/164

[56] References Cited

U.S. PATENT DOCUMENTS 5,322,903  6/1994  Bierschenk .................. 525/331.6
5,395,997  3/1995  Van Der Puy et al. ............ 570/167
5,406,008  4/1995  Sievert ........................ 570/123

FOREIGN PATENT DOCUMENTS 2081813  10/1992  Canada.

Primary Examiner—Bernard Dentz
Assistant Examiner—Charanjit S. Alilakh
Attorney, Agent, or Firm—Jay P. Friedenson

[57] ABSTRACT

The invention provides a process for production of 1,1,1,2,3,3,3-heptafluoropropane, HFC-227ea. In particular, the invention provides an inexpensive process for producing HFC-227ea in good yield by reacting 1,1,1,3,3,3-hexafluoropropane, HFC-236fa, with elemental fluorine in an inert gas.

18 Claims, No Drawings

PROCESS FOR PRODUCING 1,1,1,2,3,3,3,-HEPTAFLUOROPRANE

FIELD OF THE INVENTION

This invention relates to a process for production of 1,1,1,2,3,3,3-heptafluoropropane, HFC-227ea. In particular, the invention provides an inexpensive process for producing HFC-227ea in good yield.

BACKGROUND OF THE INVENTION

Hydrofluorocarbons ("HFC's") are of interest as potential replacements for environmentally undesirable chlorofluorocarbons and hydrochlorofluorocarbons. For example, HFC-227ea may be used in place of chlorofluorocarbon and hydrochlorofluorocarbon refrigerants and propellants.

It is known to prepare HFC-227ea through the hydrofluorination of hexafluoropropene. This process is disadvantageous, however, because hexafluoropropene is an expensive material. The process of this invention satisfies the need in the art for a process for producing HFC-227ea that overcomes the disadvantage of the prior art process.

DESCRIPTION OF THE INVENTION AND PREFERRED EMBODIMENTS

The process of the invention provides an efficient and inexpensive method for producing HFC-227ea. The method of this invention comprises reacting 1,1,1,3,3,3-hexafluoropropane, HFC-236fa, with an effective amount of elemental fluorine under conditions suitable to produce a HFC-227ea product. Optionally, the process additionally comprises the step of purifying the HFC-227ea product, which product comprises unreacted starting materials and byproducts, to recover purified HFC-227ea.

In the process of the invention, HFC-236fa is reacted in any suitable corrosion resistant vessel with elemental fluorine in an inert gas. Any suitable inert gas may be used including, without limitation, nitrogen, argon, helium, and the like. The amount of elemental fluorine used is an amount effective to achieve a greater than 5 percent conversion of the HFC-236fa to HFC-227ea. The mole ratio of HFC-236fa to elemental fluorine that may be used is from about 1:2 to about 100:1, preferably from about 1:1 to about 50:1, more preferably from about 1:1 to about 20:1. Generally, the amount of fluorine used is a concentration of fluorine in the inert gas of from about 0.1 to about 80 percent, preferably from about 1 to about 50 percent, more preferably from about 5 to about 20 percent.

The reaction of the HFC-236fa and fluorine is performed at a temperature of from about −20° to about 400° C., preferably from about 0° to about 200° C., and more preferably from about ambient temperature to about 150° C. Reaction times in a continuous process, generally, may be from about 0.1 to about 120 seconds, preferably from about 1 to about 90 seconds. In a batch process, reaction times generally may be from about 2 minutes to 72 hours, preferably from about 1 to about 48 hours, more preferably from about 5 to about 24 hours. Pressure is not critical, but the reaction is most conveniently carried out under atmospheric pressure.

The HFC-227ea product produced will contain HFC-227ea, unreacted starting materials such as HFC-236fa and elemental fluorine, as well as byproducts including, without limitation, octafluoropropane, tetrafluoromethane, and trifluoromethane. As an optional step, the HFC-227ea product may be purified by any convenient means, such as distillation, in order to separate out the unreacted starting materials and byproducts and recover purified HFC-227ea. As yet another optional step, the unreacted starting materials may be recycled to the reactor for further reaction.

The HFC-236fa used in the process of the invention is commercially available. Alternatively and preferably, the HFC-236fa may be produced by any of the known processes for producing HFC-236fa using suitable corrosion resistant vessels. These processes include the hydrofluorination of hexachloropropene and the hydrofluorination of 1,1,1,3,3,3-hexachloropropane, HCC-230. Preferably, the hydrofluorination of HCC-230 process, as disclosed in U.S. Pat. No. 5,395,997 which is incorporated herein in its entirety by reference, is used. Thus, in another embodiment, the process of the invention comprises: (A) reacting HCC-230 with an effective amount of hydrogen fluoride in the presence of a catalytic amount of a fluorination catalyst under conditions suitable to form a HFC-236fa product; (B) purifying the HFC-236fa product to recover HFC-236fa; and (C) reacting the purified HFC-236fa with elemental fluorine under conditions suitable to produce a HFC-227ea product.

In the preferred process, in which HCC-230 is hydrofluorinated in either the liquid or vapor phase, to obtain HFC-236fa, the HCC-230 is reacted with at least a stoichiometric amount, preferably from about 1 to about 10 times the stoichiometric amount, of hydrogen fluoride in the presence of a catalytic amount of a fluorination catalyst. Suitable fluorination catalysts include any inorganic metal catalysts that catalyze the substitution of fluorine for chlorine on halogenated hydrocarbons. Illustrative liquid phase catalysts include, without limitation, metal (IV) and metal (V) halides, preferably of tin, titanium, tantalum, or antimony. Suitable vapor phase catalysts include, without limitation, chromium, copper, aluminum, cobalt, magnesium, manganese, zinc, nickel and iron oxides, hydroxides, halides, oxyhalides and inorganic salts thereof, $Cr_2O_3/Al_2O_3$, $Cr_2O_3/AlF_3$, $Cr_2O_3/carbon$, $CoCl_2/Cr_2O_3/Al_2O_3$, $NiCl_2/Cr_2O_3/Al_2O_3$, $CoCl_2/AlF_3$ and $NiCl_2/AlF_3$. A catalytic amount of catalyst is used, which amount may vary depending on the catalyst as well as the process variables.

Reaction times and temperature will depend on the phase in which the reaction is carried out as well as the amount and type of catalyst. Typically, temperatures will range from about 25° to about 400° C., preferably from about 75° to 150° C. Reaction times generally range from about a few seconds to about one day. The reaction produces a HFC-236fa product that may be purified by any convenient means, such as distillation, to recover HFC-236fa for reaction with elemental fluorine to produce HFC-227ea.

The HCC-230 used to produce the HFC-236fa may be produced from the coupling reaction of carbon tetrachloride and vinylidene chloride. Therefore, in still another embodiment, the invention comprises the process of: (A) reacting carbon tetrachloride with vinylidene chloride in the presence of an effective amount of a coupling catalyst under conditions suitable to form HCC-230 product; (B) purifying the HCC-230 product to recover purified HCC-230; (C) reacting the purified HCC-230 with an effective amount of hydrogen fluoride in the presence of a catalytic amount of a fluorination catalyst under conditions suitable to form a HFC-236fa product; (D) purifying the HFC-236fa product to recover purified HFC-236fa; and (E) reacting the HFC-236fa with elemental fluorine under conditions suitable to produce a HFC-227ea product.

The carbon tetrachloride/vinylidene chloride coupling reaction may be initiated by any of several means. Initiation with metal salts is advantageous for the process of this invention. A variety of catalysts may be used including, without limitation, salts of copper or iron. Preferably, cuprous chloride, cupric chloride, or mixtures thereof are used. An effective amount of coupling catalyst is an amount sufficient to catalyze the coupling reaction. Generally at least about 0.1 mmol, preferably from about 0.1 to about 50 mmol, more preferably from about 1 to about 20 mmol of catalyst per mole of carbon tetrachloride is used. A cocatalyst may be used such as an amine, preferably in concentrations of from about 1 to about 10 moles per mole of catalyst. Suitable amine cocatalysts include, without limitation, alkanol amines, alkyl amines, and aromatic amines.

The mole ratio of carbon tetrachloride to vinylidene chloride used is at least about 2:1, preferably from about 2 to about 5:1. Temperatures for the reaction are from about 25° to about 225° C., preferably from about 80° to about 170° C., more preferably from about 125° to about 140° C. Reaction times are from about a few minutes to about 24 hours. Any solvent in which the reactants form the HCC-230 may be used. Illustrative solvents include, without limitation, acetonitrile, dimethylsulfoxide, tetrahydrofuran isopropanol, and tertiary butanol.

The invention will be clarified further by a consideration of the following non-limiting examples.

EXAMPLES

Example 1

A 150 mL pressure vessel was evacuated and 0.68 g HFC-236fa were charged into the vessel followed by 10% of $F_2$ in nitrogen charged to 55 psig. The vessel was heated to 105° C. for 24 hours. Gas chromatographic analyses of the gas mixture showed that it contained 8% HFC-227ea, 0.5% FC-218, and 1.2% of other compounds. No $F_2$ remained in the vessel.

Example 2

A 1" diameter MONEL™ pipe reactor is packed with MONEL™ mesh. HFC-236fa is fed into the reactor at about 200 sccm (standard cc per min). A 5% $F_2$/nitrogen mixture is fed into the reactor at about 2 liters per minute flow rate. The reaction zone is maintained at about 250° C. The contact time is 20 seconds. The effluent gas contains about 50% HFC-227ea in the organic mixture. HFC-236fa conversion is about 50%. The effluent gas mixture is fed into a distillation column to remove HFC-227ea in nitrogen. The unreacted HFC-236fa is recycled back into the reactor.

Example 3

0.52 g CuCl are added gradually to a mixture of 9.94 g vinylidene chloride, 58 g carbon tetrachloride, and 50 mL of acetonitrile in a 200 mL pressure bottle. The pressure bottle is immersed in an ultrathermostatic bath and equipped with a magnetic stirring bar and pressure gauge. The agitation is turned on and the bath quickly warmed to 95° C. the reaction is interrupted after 6 hours by quick cooling of the bath. The crude product, 56.16 g, is analyzed using gas chromatography and an FID detector. Analysis of the crude product indicates formation of about 23 g HCC-230, a yield of 90% based on vinylidene chloride.

Example 4

Approximately 350 lbs antimony pentachloride catalyst is charged to a 50 gal reactor. Reactor temperature is then raised to 95° C. 700 lbs/day HCC-230 made according to the process of Example 3 along 332 lbs/day HF and 36 lbs/a chlorine are fed into the reactor continuously. Chlorine is used to keep the catalyst active. The reactor pressure is maintained at about 150 psig. The product stream consists of HFC-236fa, HF, HCl and organic byproducts such as 1-chloro-1,1,3,3,3-pentafluoropropane. About 25 lbs/h pure HCl is removed from the product stream by low temperature distillation. The HCl-free product stream is then fed into a HF extraction unit to recover and recycle HF back to the reactor.

The HF-free product stream is then fed into a photochlorinator. Chlorine is added to remove the unsaturates in the presence of UV light. The final distillation of the crude HFC-236fa produces high quality HFC-236fa at 99.5% purity, the yield is about 90%.

What is claimed is:

1. A process for the production of 1,1,1,2,3,3,3-heptafluoropropane comprising the step of reacting 1,1,1,3,3,3-hexafluoropropane with an effective amount of elemental fluorine in an inert gas under conditions suitable to produce a 1,1,1,2,3,3,3-heptafluoropropane product.

2. The process of claim 1 further comprising purifying the 1,1,1,2,3,3,3-heptafluoropropane product, which product comprises unreacted starting materials and byproducts, to separate the unreacted starting materials and byproducts and recover purified 1,1,1,2,3,3,3-heptafluoropropane.

3. The process of claim 2 further comprising recycling the separated starting materials for further reaction.

4. The process of claim 1 wherein the amount of elemental fluorine used is a mole ratio of 1,1,1,3,3,3-hexafluoropropane to elemental fluorine of from about 1:2 to about 100:1.

5. The process of claim 1 wherein the reacting step is carried out at a temperature of from about −20° to about 400° C. and for a time of from about 0.1 seconds to about 72 hours.

6. The process of claim 5 wherein the reacting is carried out for a time of from about 0.1 to about 120 seconds.

7. The process of claim 5 wherein the reacting is carried out for a time of from about 2 minutes to about 72 hours.

8. A process for producing 1,1,1,2,3,3,3-heptafluoropropane comprising the steps of:

reacting 1,1,1,3,3,3-hexafluoropropane with an effective amount of elemental fluorine in an inert gas, in a mole ratio of 1,1,1,3,3,3-hexafluoropropane to elemental fluorine from about 1:2 to about 100:1, at a temperature of from about −20° to about 400° C. and for a reaction time of from about 0.1 seconds to about 72 hours, to produce a 1,1,1,2,3,3,3-heptafluoropropane product comprising 1,1,1,2,3,3,3-heptafluoropropane, unreacted starting materials and byproducts; and purifying the 1,1,1,2,3,3,3-heptafluoropropane product to separate the starting materials from the 1,1,1,2,3,3,3-heptafluoropropane and recover purified 1,1,1,2,3,3,3-heptafluoropropane.

9. The process of claim 8 further comprising recycling the separated starting materials for further reaction.

10. The process of claim 8 wherein the reacting is carried out for a time of from about 0.1 to about 120 seconds.

11. The process of claim 8 wherein the reacting is carried out for a time of from about 2 minutes to about 72 hours.

12. A process for producing 1,1,1,2,3,3,3-heptafluoropropane comprising the steps of:

reacting 1,1,1,3,3,3-hexafluoropropane with an effective amount of elemental fluorine in an inert gas, in a mole ratio of 1,1,1,3,3,3-hexafluoropropane to elemental fluorine of from about 1:1 to about 50:1, at a temperature of from about 0° to about 200° C. and for a reaction time of from about 0.1 seconds to about 72 hours, to produce a 1,1,1,2,3,3,3-heptafluoropropane product comprising 1,1,1,2,3,3,3-heptafluoropropane, unreacted starting materials and byproducts;

purifying the 1,1,1,2,3,3,3-heptafluoropropane product to separate the starting materials from the 1,1,1,2,3,3,3-heptafluoropropane and recover purified 1,1,1,2,3,3,3-heptafluoropropane; and recycling the separated starting materials for further reaction.

13. The process of claim 12 wherein the reacting is carried out for a time of from about 0.1 to about 120 seconds.

14. The process of claim 12 wherein the reacting is carried out for a time of from about 2 minutes to about 72 hours.

15. The process of claim 1, 8, or 12 further comprising the steps of preparing the 1,1,1,3,3,3-hexafluoropropane by reacting 1,1,1,3,3,3-hexachloropropane with an effective amount of hydrogen fluoride in the presence of a catalytic amount of a fluorination catalyst under conditions suitable to form a 1,1,1,3,3,3-hexafluoropropane product; and purifying the 1,1,1,3,3,3-hexafluoropropane product to recover 1,1,1,3,3,3-hexafluoropropane.

16. The process of claim 15 wherein the 1,1,1,3,3,3-hexachloropropane is reacted with at least a stoichiometric amount of hydrogen fluoride at a temperature of from about 25° to about 400° C. and for a reaction time of from about a few seconds to about one day.

17. The process of claim 15 further comprising the steps of:

preparing the 1,1,1,3,3,3-hexachloropropane by reacting carbon tetrachloride with vinylidene chloride in the presence of an effective amount of a coupling catalyst under conditions suitable to form 1,1,1,3,3,3-hexachloropropane product; and purifying the 1,1,1,3,3,3-hexachloropropane product to recover purified 1,1,1,3,3,3-hexachloropropane.

18. The process of claim 17 wherein the carbon tetrachloride and vinylidene chloride are reacted in a mole ratio of carbon tetrachloride to vinylidene chloride is from about 2:1 and at a temperature of from about 25° to about 225° C. for a reaction time of from about a few minutes to about one day in the presence of a coupling catalyst selected from the group consisting of cuprous chloride, cupric chloride, and mixtures thereof.

* * * * *